US00PP22809P3

(12) United States Plant Patent
Tellwright

(10) Patent No.: US PP22,809 P3
(45) Date of Patent: Jun. 19, 2012

(54) *NEMESIA* PLANT NAMED 'FLEURBW'

(50) Latin Name: *Nemesia×hybrida*
Varietal Denomination: FLEURBW

(76) Inventor: Martine Tellwright, Barnham (GB)

( * ) Notice: Subject to any disclaimer, the term of this patent is extended or adjusted under 35 U.S.C. 154(b) by 13 days.

(21) Appl. No.: 12/928,916

(22) Filed: Dec. 21, 2010

(65) Prior Publication Data

US 2011/0173730 P1 Jul. 14, 2011

(51) Int. Cl.
*A01H 5/00* (2006.01)

(52) U.S. Cl. ..... Plt./458

(58) Field of Classification Search ..... Plt./458
See application file for complete search history.

*Primary Examiner* — Susan McCormick Ewoldt

(57) ABSTRACT

A new and distinct cultivar of *Nemesia* plant named 'FLEURBW' that is characterized by compact habit, large fragrant bi-colored red-purple and white flowers which bloom from early spring through summer and into fall and which almost entirely cover the plant at peak flowering. In combination these characteristics set 'FLEURBW' apart from all other existing varieties of *Nemesia* known to the inventor.

2 Drawing Sheets

Genus: *NEMESIA*.
Species: ×*hybrida*.
Denomination: 'FLEURBW'.

BACKGROUND OF THE INVENTION

This application claims the benefit of priority under 35 U.S.C. 119(f) of the application for a grant of European Community Plant Variety Rights which was filed for the instant plant variety on Jan. 14, 2010, File Number 2010/0085.

The present invention relates to a new and distinct cultivar of *Nemesia* plant that is grown as an ornamental plant for use in the garden border, in patio containers or in the landscape. The new cultivar is known botanically as *Nemesia×hybrida* and will be referred to hereinafter by the cultivar name 'FLEURBW'.

'FLEURBW' resulted from a formal breeding program begun by the inventor in 1998 at her nursery in West Sussex, United Kingdom. The purpose of the breeding program is to produce new varieties of *Nemesia* that exhibit compact habit and new flower colors and color combinations.

In 2004, the inventor conducted controlled cross-pollination between the inventor's variety of *Nemesia* plant named 'FLEURBAC" (U.S. Plant Pat. No. 16,931) as male parent, and an unnamed and unreleased seedling raised by the inventor as female parent. This cross-pollination produced many seedlings from which the inventor selected 'FLEURBW'. The inventor selected 'FLEURBW' for the attractiveness and uniqueness of its bi-colored flowers whose upper lip is bright red-purple in color and which contrasts with the predominantly clear white color of the lower lip of the flowers. In addition, the inventor was attracted to the tidy compact form of the new seedling and the amount of bloom at peak flowering.

'FLEURBW' may be compared with the bi-colored male parent, 'FLEURBAC'. 'FLEURBAC' is also the closest comparison variety known to the inventor, since both 'FLEURBAC and 'FLEURBW' are bi-colored and have a compact habit. However, whereas the upper lip of the flower of 'FLEURBAC' is violet-blue in color, the upper lip of 'FLEURBW' is red-purple in color.

'FLEURBW' may be compared with the unreleased female parent as follows: Whereas the upper lip of the flower of 'FLEURBW' is red-purple in color and the lower lip of 'FLEURBW' is white, the upper and lower lips of the female parent are pink and pale pink respectively.

'FLEURBW' may also be compared with another of the inventor's varieties, 'FLEURRAS' (unpatented). Both 'FLEURBW' and 'FLEURRAS' exhibit red-purple (upper lip) and white (lower lip) bi-colored flowers. The flowers of 'FLEURBW" exhibit significantly less "bleeding" of color from upper lip to lower lip which results in an almost entirely white lower lip. In addition, the plant height of 'FLEURRAS' is approximately 25% greater than the height of 'FLEURBW'.

'FLEURBW' was first asexually propagated by the inventor in 2004 in a cultivated area of West Sussex, United Kingdom using softwood cuttings. The inventor has determined that the distinguishing characteristics of 'FLEURBW' are stable and are reproduced true to type in successive generations of asexual propagation.

SUMMARY OF THE INVENTION

The following traits have been repeatedly observed and represent the distinguishing characteristics of 'FLEURBW'. In combination these traits set the new cultivar apart from all other existing varieties of *Nemesia* known to the inventor. 'FLEURBW' has not been tested under all possible conditions and phenotypic differences may be observed with variations in environmental, climatic, and cultural conditions, however, without any variance in genotype.

1. 'FLEURBW' exhibits upright compact habit.
2. 'FLEURBW' exhibits large fragrant bi-colored flowers.
3. The upper lip of the flower of 'FLEURBW' is red-purple in color.
4. The lower lip of the flower of 'FLEURBW' is predominantly or completely white in color with little "bleeding" of the red-purple color from the upper lip.

5. 'FLEURBW' blooms from early spring through summer and into fall.
6. At peak flowering, the foliage of 'FLEURBW' is almost entirely covered with flowers.
7. 'FLEURBW' achieves a height and spread of approximately 16 cm in its first season of growth from a cutting.
8. 'FLEURBW' sets few seeds.
9. 'FLEURBW' is hardy and perennial in USDA Zone 8 regions and warmer.

BRIEF DESCRIPTION OF THE DRAWINGS

The accompanying color drawings illustrate the overall appearance of the new *Nemesia* cultivar 'FLEURBW' showing the colors as true as it is reasonably possible to obtain in colored reproductions of this type. Colors in the drawings may differ from the color values cited in the detailed botanical description, which accurately describe the actual colors of the new variety 'FLEURBW'. The drawings are made of nine months old plants which have been grown in 1 liter containers in a frost-protected greenhouse in West Sussex, United Kingdom.

The drawing labeled as FIG. 1 depicts a whole plant of 'FLEURBW' at its peak of flowering.

Figure 1:
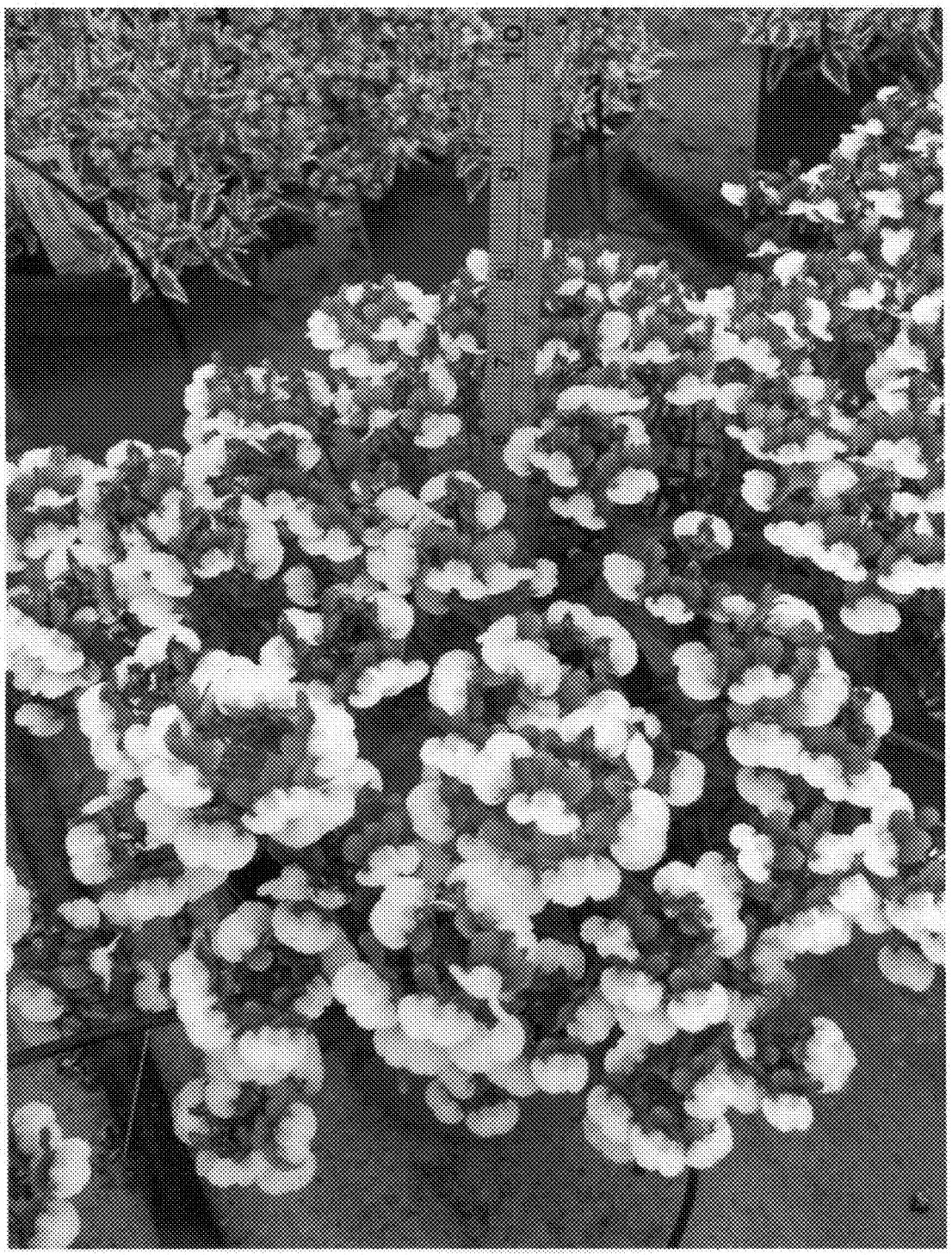
Figure 2:
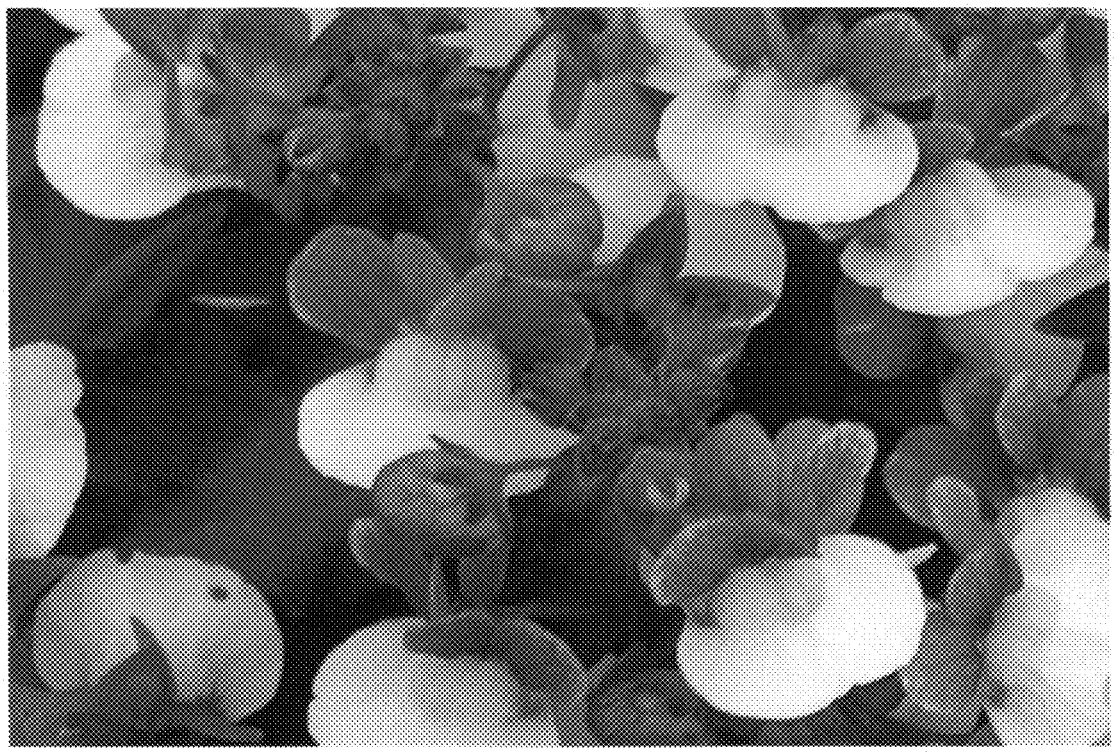

The drawing labeled as FIG. 2 depicts a close-up view of the bi-colored flowers of 'FLEURBW'.

DETAILED BOTANICAL DESCRIPTION

The following is a detailed description of 'FLEURBW' which has been compiled from records and observations of plants grown by the inventor in West Sussex, United Kingdom. Data and descriptions have been taken from nine months old plants which have been grown in a cool greenhouse in 1 liter containers. No growth regulators have been used. Phenotypic differences may be observed with variations in environmental, climatic, and cultural conditions. The color determinations are in accordance with the 2007 Edition of The Royal Horticultural Society Colour Chart, except where general color terms of ordinary dictionary significance are used.

Botanical classification: *Nemesia×hybrida* 'FLEURBW'.
Genus: *Nemesia.*
Species: *×hybrida.*
Denomination: 'FLEURBW'.
Commercial classification: Ornamental.
Common name: *Nemesia.*
Suggested uses: For use in the garden border, in patio containers or in the landscape.
Suggested commercial container size: 9 cm or 1-liter containers.
Cultural needs: Full sun, moist well-draining soil or peat-based medium, and application of a general plant fertilizer during the growing season.
Parentage: 'FLEURBW' resulted from the cross-pollination of the following parent plants:
  *Male parent.*—*Nemesia* 'FLEURBAC'.
  *Female parent.*—Unnamed and unreleased seedling of *Nemesia.*
Propagation: Softwood cuttings.
Growth Habit: Upright, compact habit.
Vigor: Vigorous.
Plant dimensions: 16 cm. in height and 16 cm. in width when grown to flowering in a 1-liter container.
Type: Perennial in USDA Zone 8 and warmer. Annual in colder regions.
Seasonal interest: Blooms in spring with bi-colored flowers that are red-purple and white in color. The bright yellow palate of each flower is considered an attractive feature.
Time to initiate roots: Approximately 14 days are needed to develop roots on initial cuttings.
Temperatures to initiate rooting: The air temperature that is recommended for rooting is 16° Celsius and the soil temperature that is recommended for rooting is 24° Celsius.
Crop time (from planting a rooted cutting): Approximately 8 weeks to produce a finished 9 cm. container plant in bud and first flower, and 3 months to produce a finished flowering 1-liter container plant after one pinch.
Root system: Fine.
Hardiness: Hardy to minus 6° Celsius or USDA Zone 8.
Disease and pest susceptibility: 'FLEURBW' is susceptible to viruses and whitefly.
Special growing requirements:
  *Pruning.*—Pinch back when potted from plug to commercial container.
  *Growing medium.*—Well-drained peat based medium is recommended.
  *Light.*—Normal daylight.
Growing problems: None known to the inventor.
Stem:
  *Stem shape.*—Quadrate.
  *Stem length.*—10 cm-15 cm.
  *Stem diameter.*—2 mm-3 mm in diameter.
  *Stem surface.*—Glabrous.
  *Stem color.*—137D.
  *Pubescence.*—None.
  *Internode length.*—12 mm-15 mm.
  *Branching habit.*—Pinching stimulates basal and axillary branching.
Foliage:
  *Leaf arrangement.*—Opposite.
  *Type.*—Evergreen.
  *Leaf shape.*—Oval.
  *Leaf division.*—Simple.
  *Apex.*—Acute.
  *Base.*—Rounded.
  *Margins.*—Dentate.
  *Surface.*—Glabrous.
  *Leaf pubescence.*—None observed.
  *Leaf length.*—2 cm-3 cm.
  *Leaf width.*—7 mm-12 mm.
  *Leaf color* (*both surfaces*).—137A.
  *Leaf attachment.*—Petiolate.
  *Petiole shape.*—Sulcate.
  *Petiole surface.*—Glabrous.
  *Petiole dimensions.*—3 mm-5 mm in length and 1.5 mm-2.0 mm in width.
  *Petiole color.*—137A.
  *Vein pattern.*—Pinnate.
  *Vein color.*—As leaf lamina, 137A.
Flowers:
  *Flowering season.*—Spring.
  *Fragrance.*—Strongly perfumed with vanilla-like scent.
  *Self-cleaning or persistent.*—Self-cleaning.
  *Type of inflorescence.*—Corymb.
  *Number of corymbs per plant.*—Initially few, increasing to 40-50 at peak flowering.
  *Number of flowers per corymb.*—From 2-4 initially, increasing to 10-15.
  *Number of flowers per plant.*—Very many, in the region of 500 individual flowers at peak flowering.

*Peduncle dimensions.*—2.0 cm-2.5 cm in length; 1.5 mm-2.0 mm in diameter.
*Peduncle shape.*—Quadrate.
*Peduncle surface.*—Glabrous.
*Peduncle color.*—139B.
*Pedicel dimensions.*—8 mm-10 mm in length; 0.5 mm-1.0 mm. in diameter.
*Pedicel shape.*—Quadrate.
*Pedicel surface.*—Glabrous.
*Pedicel color.*—139C.
*Bud shape.*—Globular.
*Bud color.*—Emerges 157D, becoming 158A immediately prior to opening.
*Bud surface.*—Glabrous.
*Bud dimensions.*—7 mm. in diameter immediately prior to opening.
*Quantity of buds.*—Up to 15 buds per corymb.
*Flower shape.*—Corolla personate with single spur (pouch) at the base.
*Flower dimensions.*—2 cm in length and 2 cm in width.
*Flower color.*—The following colors are all individually present on each flower: Upper lip: 61C, 58A and 73D. Lower lip: Pure white (lighter than any color chart reading), 8A, 61C.
*Corolla tube dimensions.*—6 mm. in length; 2 mm. in diameter.
*Corolla tube color.*—Inner surface: 155A. Outer surface: Ranges between 155C and 158D.
*Palate* (*pollinator landing platform*).—Shape: Rectangular bifid protuberance. Dimensions (entire palate): 5 mm in length; 3 mm in width. Color: 8A.
*Upper lip.*—Lip dimensions overall: 15 mm in width and 5 mm in height. Lobes: Upper lip comprised of 4 basally fused lobes. Lobe dimensions: 4 mm-5 mm in width; 4 mm-5 mm in height. Lobe apex: Rounded. Lobe base: Gently cordate. Lobe margins: Entire. Lobe surface: Glabrous. Lobe color (as lip): 61C with darker veins 58A and pale pink margins 73D.
*Lower lip* (*entire*).—Dimensions: 15 mm in width; 10 mm in height Apex: Emarginate. Base: Attenuate and forming mouth of nectar tube (spur). Margins: Entire. Surface: Glabrous. Color: Pure white ground (lighter than any color chart reading) on which lemon-yellow palate 8A, small (approximately 2 mm×2 mm) patches of red-purple 61C.
*Nectary* (*spur*).—Shape: Cylindrical, slightly reflexed away from lower lip. Dimensions: 3 mm-5 mm in length; 1.0 mm-1.5 mm in diameter, tapering towards rounded apex. Color: 163C.
*Calyx shape.*—Palmate with 5 basally fused sepals.
*Sepal surface.*—Glabrous.
*Sepal apex.*—Acute.
*Sepal margin.*—Entire.
*Sepal dimensions.*—3 mm. in length and 1 mm. in width.
*Sepals fused or unfused.*—Unfused.
*Sepal color* (*both surfaces*).—137B becoming darker 147A toward apex.
*Lastingness of individual flower.*—An individual flower lasts 7-10 days.

Reproductive organs:
*Stamens.*—Two in number.
*Color of stamens.*—155A.
*Stamen dimensions.*—2 mm. in length and less than 0.25 mm. in diameter.
*Anther color.*—5C.
*Amount of pollen.*—Moderate.
*Pollen color.*—5C.
*Anther dimensions.*—1 mm. in length and less than 0.50 mm. in width.
*Pistil.*—One.
*Pistil color.*—144D.
*Pistil dimensions.*—1 mm. in length and 0.25 mm. in diameter.
*Ovary.*—Superior, globular, less than 0.50 mm. in height and diameter, pale green in color.
*Seed.*—Sparse, flattened oval, 2 mm in length, 1.25 mm in width, mid-brown in color.

The invention claimed is:

1. A new and distinct cultivar of *Nemesia* plant named 'FLEURBW' as described and illustrated herein.

* * * * *